US011105790B2

(12) United States Patent
Morley et al.

(10) Patent No.: US 11,105,790 B2
(45) Date of Patent: Aug. 31, 2021

(54) COMPOSITIONS AND METHODS FOR DIAGNOSING PARASITIC INFECTIONS

(71) Applicant: ZOMEDICA CORP., Ann Arbor, MI (US)

(72) Inventors: Stephanie Morley, Ann Arbor, MI (US); Casey Wegner, Ann Arbor, MI (US)

(73) Assignee: Zomedica Corp., Ann Arbor, MI (US)

( * ) Notice: Subject to any disclaimer, the term of this patent is extended or adjusted under 35 U.S.C. 154(b) by 0 days.

(21) Appl. No.: 16/696,028

(22) Filed: Nov. 26, 2019

(65) Prior Publication Data

US 2021/0156839 A1 May 27, 2021

(51) Int. Cl.
*G01N 33/483* (2006.01)
*G01N 21/65* (2006.01)
*G16C 20/70* (2019.01)

(52) U.S. Cl.
CPC ....... *G01N 33/4833* (2013.01); *G01N 21/658* (2013.01); *G16C 20/70* (2019.02); *G01N 2201/126* (2013.01)

(58) Field of Classification Search
CPC ............. G01N 33/4833; G01N 21/658; G01N 2201/126; G16C 20/70
See application file for complete search history.

(56) References Cited

U.S. PATENT DOCUMENTS

| 8,145,295 | B2* | 3/2012 | Boyden | A61N 5/0624 600/476 |
| 2016/0145327 | A1* | 5/2016 | Geng | C07K 16/18 435/7.93 |
| 2016/0177366 | A1* | 6/2016 | Auner | G01N 21/65 435/5 |
| 2016/0273033 | A1* | 9/2016 | Gold | C12Q 1/6869 |
| 2020/0264050 | A1* | 8/2020 | Auner | G01N 21/65 |

OTHER PUBLICATIONS

Cortes, C., et al. Machine Learning, 1995; 20 (3): 273-297.
Ho, Tin Kam. Random decision forests. Proceedings of the 3rd International Conference on Document Analysis and Recognition, Montreal, QC, 1995; Aug. 14-16, 1995. pp. 278-282. Abstract only.
Ho, Tk. The Random Subspace Method for Constructing Decision Forests. IEEE Transactions on Pattern Analysis and Machine Intelligence, 1998; 20 (8): 832-844. Abstract only.

* cited by examiner

*Primary Examiner* — Jamil Ahmed
(74) *Attorney, Agent, or Firm* — Casimir Jones, S.C.; Tanya A. Arenson

(57) ABSTRACT

Provided herein are compositions and methods for diagnosing parasitic infections. In particular, provided herein are compositions and methods for preparing samples (e.g., canine fecal samples) and performing Raman spectroscopy detection of parasites infections in the samples.

16 Claims, 6 Drawing Sheets

Infected and uninfected canine feces

Fecal sample dilutions or flotations

Raman Spectroscopy Device Interrogation of Sample

Raman Spectra Preprocessing
(Morphology-Split background subtraction, Unit Vector Normalization)

Machine Learning
(SVM or Random Forest)

Identify and Classify Biomarker Signature

COMPOSITIONS AND METHODS FOR DIAGNOSING PARASITIC INFECTIONS

FIELD OF THE DISCLOSURE

Provided herein are compositions and methods for diagnosing parasitic infections. In particular, provided herein are compositions and methods for preparing samples (e.g., canine fecal samples) and performing Raman spectroscopy detection of parasites infections in the samples.

BACKGROUND OF THE DISCLOSURE

Many parasites can infect the digestive system of dogs. Some gastrointestinal parasites of dogs can also cause disease in humans. Parasites, particularly intestinal worms such as hookworms, tapeworms and roundworms, can be transmitted in a dog's feces. Some tapeworms have fleas as intermediate hosts: the worm egg must be consumed by a flea to hatch, then the infected flea must be ingested (usually by the dog while grooming itself, but occasionally by a human through various means) for the adult worm to establish itself in the intestines. The worm's eggs then pass in the feces, and the cycle begins again. Intestinal worms cause varying degrees of discomfort.

Besides being hard to detect, many dogs infected with intestinal parasites are asymptomatic. Even symptomatic dogs may go undetected because their symptoms can be nonspecific. The most common signs and symptoms of intestinal parasites are scooting, vomiting, diarrhea, a distended abdomen, weight loss, and occasionally coughing.

Although intestinal parasites are treatable, since dogs infected with intestinal parasites can exhibit no symptoms or subtle symptoms that can be easily overlooked, the best way to ensure that a dog is parasite-free is testing. However, existing testing methods are slow and cumbersome.

What is needed are rapid and efficient methods for detection of parasitic infections in dogs, preferably at the point of care.

SUMMARY OF THE DISCLOSURE

Provided herein are compositions and methods for diagnosing parasitic infections. In particular, provided herein are compositions and methods for preparing sample (e.g., non-human mammals, e.g., canine samples (e.g., fecal samples)) and performing Raman spectroscopy detection of parasites infections in the samples.

The compositions, systems, and methods of the present disclosure provide rapid, point of care detection of parasitic infections in canine samples. The detection methods provide multi-omic, multiplex detection without the need for costly and time-consuming reagents and complicated sample preparation. The described methods result in improved care of canine subjects with parasitic infections.

For example, in some embodiments, provided herein is a method of identifying the presence of a parasite in a sample (e.g., urine or fecal sample) from a canine, comprising: a) diluting the sample with water to generate a diluted sample; and b) obtaining a Raman spectrum of the sample using a Raman spectrometer, wherein the Raman spectrum identifies the presence of a parasite in the sample. The methods described herein allow for detection of parasites in small sample sizes (e.g., less than 1000, 500, 200, or 100 mg of feces). In some embodiments, the presence of a parasite in the sample is determined based on the presence of coproantigen and/or parasite lifecycle signatures (e.g., molecular markers) in the sample.

The present disclosure is not limited to detection of particular parasites. Examples include, but are not limited to, hookworm, roundworm, *Cystoisospora*, *Giardia*, or whipworm.

The present disclosure is not limited to particular Raman spectroscopy methods. In some embodiments, the Raman spectroscopy utilizes internal reflective amplification. In some embodiments, the Raman spectroscopy generates a molecular fingerprint of the sample (e.g., comprising spectral bands indicative of one or more of proteins, nucleic acids, carbohydrates, or small molecules. In some embodiments, the molecular fingerprint identifies the genus, species, or strain of parasite in the sample.

In some embodiments, the Raman spectrum are analyzed using a machine learning algorithm (e.g., random forest (RF) and/or support vector machines (SVM)). In some embodiments, spectra are preprocessed prior to analysis (e.g., one or more of morphology-split background subtraction and unit vector normalization). In some embodiments, the method further comprises generating a receiver operating characteristic curve (ROC) for multiple classes. In some embodiments, the ROC comprises a micro-averaging step.

In some embodiments, the Raman spectrometer is a portable Raman spectrometer. In some embodiments, the Raman spectrometer is battery operated or AC operated. In some embodiments, the Raman spectrometer comprises a plurality of filters that filter the spectral band of the spectrometer to specific wavelengths or wavelength bands of light. In some embodiments, the Raman spectrometer is automated (e.g., including obtaining spectrum and analyzing data). In some embodiments, the Raman spectrometer performs spectroscopy and analysis in 5 minutes (e.g., 5, 4, 3, 2, or 1 minute) or less. In some embodiments, the method is performed at the point of care (e.g., at a veterinary clinic).

Further embodiments provide a method of treating a canine subject for a parasitic infection, comprising: detecting the presence of a parasitic infection using a method as described herein; and administering an antibiotic to the canine. In some embodiments, the method is repeated one or more times by retesting a new sample after administration of the antibiotic to the canine (e.g., to monitor treatment). In some embodiments, one or more antibiotics are selected based on the identity of the infectious disease agent identified.

Additional embodiments provide a system or kit comprising: a) a diluted (e.g., diluted with water) fecal mixture from a subject; and b) a Raman spectrometer. In some embodiments, the subject is suspected of having a parasitic infection. In some embodiments, the Raman spectrometer comprises: i) a library of Raman spectrometric signatures from antigens from parasites, and ii) an algorithm for comparing a Raman spectrometric signature from the sample to the library. In some embodiments, the kit or system further comprises a computer system comprising a computer memory and computer processor, wherein the computer memory comprises a library of Raman spectrometric signatures from antigens from parasites, and algorithm for comparing a Raman spectrometric signature from said sample to the library, wherein the computer system is operably linked to the Raman spectrometer.

Yet other embodiments provide a system comprising: a) a Raman spectrometer, wherein the Raman spectrometer is configured to generate a test spectra from a diluted fecal sample; and b) a computer system comprising: i) a computer processor, and ii) non-transitory computer memory comprising one or more computer programs and a database, wherein the one or more computer programs comprise: a comparison algorithm, and wherein the database comprises a plurality of Raman spectra from fecal parasites, wherein the one or more computer programs, in conjunction with said computer processor, is/are configured to apply the algorithm to determine the identity of test spectra based on comparison to the plurality of Raman spectra in the database. In some embodiments, the computer system is part of, separate, or in operable communication with the Raman spectrometer.

Additional embodiments are described herein.

DESCRIPTION OF THE FIGURES

The patent or application file contains at least one drawing executed in color. Copies of this patent or patent application publication with color drawings will be provided by the Office upon request and payment of the necessary fee.

DEFINITIONS

Figure 1A:
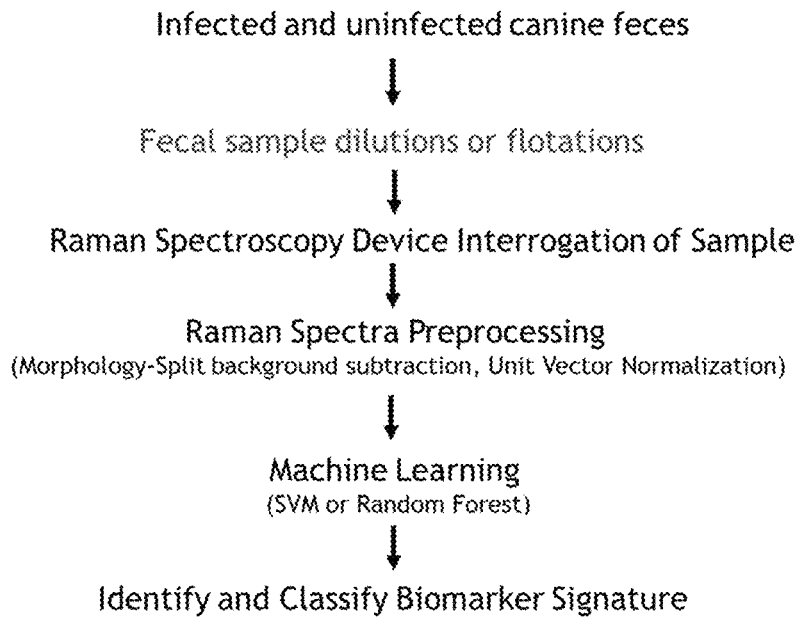
FIG. 1A shows a schematic of an exemplary workflow of methods of embodiments of the present disclosure.

As used herein, the terms "detect", "detecting", or "detection" may describe either the general act of discovering or discerning or the specific observation of a composition.

The term "sample" as used herein is used in its broadest sense. In one sense it can refer to a biological sample. Biological samples may be obtained from animals (e.g., mammals, including companion animals such as canines, felines, and the like) and encompass fluids, solids, tissues, and gases. Biological samples include, but are not limited to feces, urine and blood products, such as plasma, serum and the like. These examples are not to be construed as limiting the sample types applicable to the present disclosure.

DETAILED DESCRIPTION OF THE DISCLOSURE

Provided herein are compositions and methods for diagnosing parasitic infections. In particular, provided herein are compositions and methods for preparing samples (e.g., canine fecal samples) and performing Raman spectroscopy detection of parasites infections in the samples.

By combining multi-omic detection with rapid, portable or small bench top instruments, and integrated data analysis components, the methods of the present disclosure provide both diagnostic information (e.g., the presence of a parasitic infection), and further information regarding the genus, species, or strain of parasite present. This results in improved antibiotic stewardship by veterinarians due to genus and species-level detection at the time of an initial patient visit.

Previous assays for parasitic infections include ELISA testing, PCR, microscopy, and fecal flotation methods. ELISA is an enzyme-linked immunosorbent method that offers a rapid and sensitive method to determine the presence of parasites by detecting excretory-secretory coproantigens secreted by the mature parasites. This test proved to be highly sensitive and specific, allowing for fast large mass screening capacity. However, ELISA testing requires the availability of specialized equipment and is subject to cross-reaction between antibodies from one parasite protein and proteins from other species. ELISA POC testing is currently only offered as a lateral flow assay, so it cannot provide a precise evaluation when needed at POC settings.

PCR technology quantifies DNA and RNA, and is best-suited for parasite detection in veterinary medicine and is predominantly a reference lab technology. Its sensitivity permits enzymatic amplification of gene fragments from nucleic acids derived from certain parasite material. While there are some point of care PCR platforms, they have significant limitations in workflow that require technical skill sets above those commonly found in a veterinary clinic. PCR technologies are expensive and labor-intensive. Often no suitable DNA sequences are available for one specific organism, which requires lab techniques to use nested PCR assays to increase sensitivity and specificity. Additionally, modifications of external factors, such as the concentration of reaction components, temperature, and duration of each reaction step, influence the detection of the results. PCR also suffers from a lack of standardization since many factors, including DNA extraction methods, choice of primer sets, and use of amplification protocols may lead to diversification in results. PCR technology is currently only offered at reference labs in veterinary medicine, takes 1-3 days to get results, and has limitations on multiplexing and automation abilities for POC applications. Another flaw associated with result interpretation in PCR is detected dead organism, which can produce false positives.

Microscopy is the evaluation of fecal material using a microscope in both automated (e.g., use of a high-powered camera with advanced imaging software) and non-automated environments (e.g., a veterinary technician). Fecal sedimentation analysis, fixed fecal smear and Baermann test are used to identify parasite larvae or eggs, based on characteristics of motility, structure and/or color of stains. Microscopic exam requires experienced technicians to add fecal material to a microscope slide and examine the slide to identify parasite eggs based on motility, structure and/or color of stains via microscopy. High levels of parasite are usually required for good sensitivity. This is a highly subjective process that results in human error and a high degree of variability since technicians cannot distinguish between morphologically similar organisms. In addition, microscopic exam may underdiagnose the disease as intermittent cyst shedding leads to false negative results. Therefore, multiple fecal samples need to be collected and examined in order to increase the sensitivity of diagnosis. Microscopic exam requires lab technicians to handle potentially infectious fecal material. The fecal sample is also required to incubate for certain amount of time prior to further examination, which could lead to a workflow interference and delay in treatment.

Fecal flotation/centrifugation is a process that places a patient sample (e.g. fecal material) into a container and mixes it with a special solution. The eggs of many parasites will float to the top of the container and get collected with a microscope coverslip. After a few minutes, the cover slip will be ready for microscopic analysis and identification of eggs by a technician. Fecal centrifugation uses the same flotation techniques, but the sample is placed into a centrifuge to enhance detection of parasite eggs. Fecal flotation/centrifugation allows a basic screening to detect parasites when sample size is small. A fecal flotation test may fail to detect parasite infection if 1) the parasites are too young to produce eggs; 2) the infection is mild and only a few adult parasites are present; 3) some parasites only produce limited numbers of eggs; 4) eggs of certain parasites are too heavy to float or 5) flotation medium distorts or ruptures eggs/larvae. Fecal centrifugation also requires the availability of specialized equipment (e.g. centrifuge) and requires lab technicians to handle potentially infectious fecal material.

Raman spectroscopy, discovered by physicist Sir C. V. Raman, has been utilized for decades in the research setting, but several limitations prevented clinical/diagnostic application of Raman spectroscopy. These limitations include lack of a Raman method to facilitate real-time, point of care application; lack of ability to miniaturize Raman devices without sacrificing performance, to have an acceptable footprint for point of care use (corresponds with much lower device cost); lack of automated Raman-based detection of targets in biological samples with no user analysis or interpretation required; rapid microbe genus, species and strain level detection at the point of care; rapid genus, species and strain level detection multiplexing at the point of care; rapid parasite detection techniques that do not rely on flotation or microscopic analysis; the need for rapid parasite detection based on multi-omic information at the point of care, not just molecular vs protein vs cellular detection; the need for parasite detection technology at the point of care that does not require time-consuming sample processing (sample prep) protocols; and improved antibiotic stewardship practices at the point of care based on the ability to identify parasite genus, species and strains in real time.

A number of Raman spectroscopy techniques, for example, Raman microspectroscopy, selective-sampling Raman microspectroscopy, coherent anti-Stokes Raman spectroscopy (CARS), surface enhanced Raman spectroscopy (SERS), fiber-optic Raman probes, and resonance Raman scattering (RRS) have been developed. However, each of these techniques have limitations that make them inadequate for use in the point of care setting.

The present disclosure addresses these needs by providing an analysis method that, in some embodiments, utilizes portable, automated Raman spectroscopy suitable for point of care parasite detection, treatment and management.

The Raman spectroscopy methods described herein provide the advantage of simple sample preparation (e.g., dilution of a fecal sample with water). In addition, the methods described herein require a much smaller sample size than other fecal detection methods, which frequently require several grams of sample. For example, in some embodiments, methods described herein utilize less than 1000 mg of fecal sample (e.g., less than 500, 200, or 100 mg of sample)

After sample preparation, samples are analyzed using Raman spectroscopy. The present disclosure is not limited to particular Raman spectrometers. In some embodiments, commercially available Raman spectrometry systems are utilized. (See also U.S. Pat. No. 10,253,346, and U.S. patent application Ser. No. 16/451,901; each of which is herein incorporated by reference in its entirety).

In some embodiments, Raman spectrometers for use in the described methods are portable (e.g., light weight, table top instruments). In some embodiments, portability is enhanced by powering the instrument with a disposable or rechargeable battery. In some embodiments, instruments run on AC. In some embodiments, Raman spectrometers utilize filters to restrict spectrum to a single or narrow range of bandwidths.

In some embodiments, the Raman spectroscopy methods described herein utilize automated detection (e.g., generation of spectrum and analysis of spectrum). In some embodiments, algorithms and pathogen libraries are embedded in the system's onboard software to achieve automated analysis and output information. In other embodiments, such algorithms and libraries are part of a computer system (e.g., with computer memory and a computer processor) in communication with the Raman spectrometer.

In some embodiments, the Raman spectroscopy is rapid (e.g., less than 5, 4, 3, 2, or 1 minute, including or not including data analysis).

In some embodiments, assays identify coproantigen and/or parasite lifecycle signatures (e.g., multi-omic molecular signatures) in the sample. In some embodiments, antigens are secretory/excreted product such as coproantigens. Coproantigens are antigens from parasites that are shed in feces. Exemplary Giardia antigens are described, for example in Ghoshal et al., Pathogens and Global Health, 110:316; herein incorporated by reference in its entirety). Exemplary roundworm, whipworm, and hookworm antigens are described, for example, in U.S. Pat. No. 10,429,388; herein incorporated by reference in its entirety.

In some embodiments, the Raman spectroscopy methods described herein utilize multi-omic information to generate a molecular fingerprint indicative of disease. For example, in some embodiments, a single Raman spectrum comprises peaks related to the presence of one or more of proteins, nucleic acids (e.g., DNA and/or RNA), carbohydrates, and small molecules (e.g., metabolites) indicative of the presence of a parasite in the sample.

In some embodiments, Raman spectroscopy methods described herein identify the presence of parasites in a subject (e.g., a canine subject). For example, in some embodiments, Raman spectroscopy identifies the presence and/or genus, species, and strain of parasite. The present disclosure is not limited to detection of particular parasites. Examples include, but are not limited to, hookworm, roundworm, *Cystoisospora, Giardia,* or whipworm.

The present disclosure is not limited to particular subjects. In some embodiments, the subject is a mammal (e.g., non-human mammal). In some embodiments, the subject is a companion animal (e.g., dog, cat, horses, rabbits, ferrets, birds, guinea pigs and other small mammals, small reptiles and fish). In some embodiments, the subject is a canine subject.

In some embodiments, the Raman spectroscopy systems described herein utilize a machine learning algorithm for data analysis. Machine learning algorithms build a mathematical model based on sample data, known as "training data", in order to make predictions or decisions without being explicitly programmed to perform the task. In some embodiments, machine learning algorithms utilize support-vector machines and/or random forest algorithms.

In machine learning, support-vector machines (SVMs, also support-vector networks; Cortes, Corinna; Vapnik, Vladimir N. (1995). Machine Learning. 20 (3): 273-297; herein incorporated by reference in its entirety) are supervised learning models with associated learning algorithms that analyze data used for classification and regression analysis. Given a set of training examples, each marked as belonging to one or the other of two categories, an SVM training algorithm builds a model that assigns new examples to one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall.

analysis, the treatment is stopped (e.g., when no further symptoms of disease are identified) or altered (e.g., when symptoms of disease are still present after a treatment course). The analysis is repeated as many times as needed prior to, during, or after treatment.

The below Table provides a list of exemplary antibiotics for use with specific parasites. C:cat; D:dog; B:both

| Parasite | Therapeutic | Albendazole | Emodepside | Eprinomectin | Febantel | Fenbendazole | Furazolidone | Ipronidazole | Ivermectin | Metronidazole |
|---|---|---|---|---|---|---|---|---|---|---|
| Cystoisospora | Recommended First Line | | | | | | | | | |
| Giardia | Recommended First Line | B | | | | B | C | D | | B |
| Hookworm | Recommended First Line | | B | | | | | | B | |
| Roundworm | Recommended First Line | | C | C | D | B | | | | |
| Whipworm | Recommended First Line | | | | B | B | | | | |

| Parasite | Therapeutic | Milbemycin oxime | Moxidectin | Piperazine | Pyrantel pamoate | Pyrantel, praziquantel, febantel | Quinacrine | Ronidazole | Selamectin | Sulfadimethoxine | Tinidazole |
|---|---|---|---|---|---|---|---|---|---|---|---|
| Cystoisospora | Recommended First Line | | | | | | | | | B | |
| Giardia | Recommended First Line | | | | | B | B | C | | | B |
| Hookworm | Recommended First Line | B | B | | | | | | B | | |
| Roundworm | Recommended First Line | B | B | B | B | | | | C | | |
| Whipworm | Recommended First Line | | | | | | | | | | |

Random forests or random decision forests are an ensemble learning method for classification, regression and other tasks that operates by constructing a multitude of decision trees at training time and outputting the class that is the mode of the classes (classification) or mean prediction (regression) of the individual trees (See e.g., Ho, Tin Kam (1995) Proceedings of the 3rd International Conference on Document Analysis and Recognition, Montreal, QC, 14-16 Aug. 1995. pp. 278-282; Ho TK (1998) IEEE Transactions on Pattern Analysis and Machine Intelligence. 20 (8): 832-844; each of which is herein incorporated by reference in its entirety).

In some embodiments, spectra are preprocessed prior to analysis (e.g., one or more of morphology-split background subtraction and unit vector normalization).

In some embodiments, the method further comprises generating a receiver operating characteristic curve (ROC) for multiple classes. In some embodiments, the ROC comprises a micro-averaging step.

The methods of the present disclosure provide for rapid, point of care diagnosis, prognosis, and patient monitoring applications. Embodiments of the disclosure provide methods for determining a treatment course of action, administering a treatment, and/or monitoring a treatment. For example, in some embodiments, the results of the analysis methods described herein are used to select an initial antibiotic based on the type of parasite present in a sample. Following administration of the antibiotic to the subject, in some embodiments, analysis is repeated one or more times by retesting a new sample after administration of the antibiotic to the canine to determine the efficacy of the antibiotic. In some embodiments, based on the results of the

EXPERIMENTAL

The following example is provided in order to demonstrate and further illustrate certain preferred embodiments and aspects of the present disclosure and are not to be construed as limiting the scope thereof.

Example 1

This Example describes methods of using Raman spectroscopy to detect parasitic infections at the point of care. FIG. 1A shows a schematic of the methodology used. Table 1 shows the number of Raman Device Runs for Each Sample. Data was split into 70% training and 30% testing (validation) data sets.

Figure 1B:
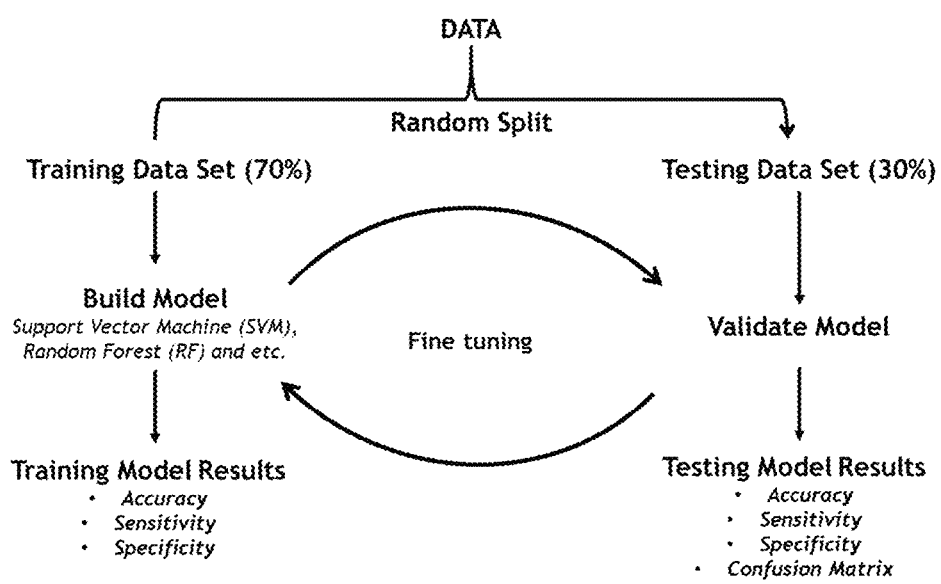
FIG. 1B shows a schematic of an exemplary workflow of methods of data analysis used embodiments of the present disclosure.
Figure 2:
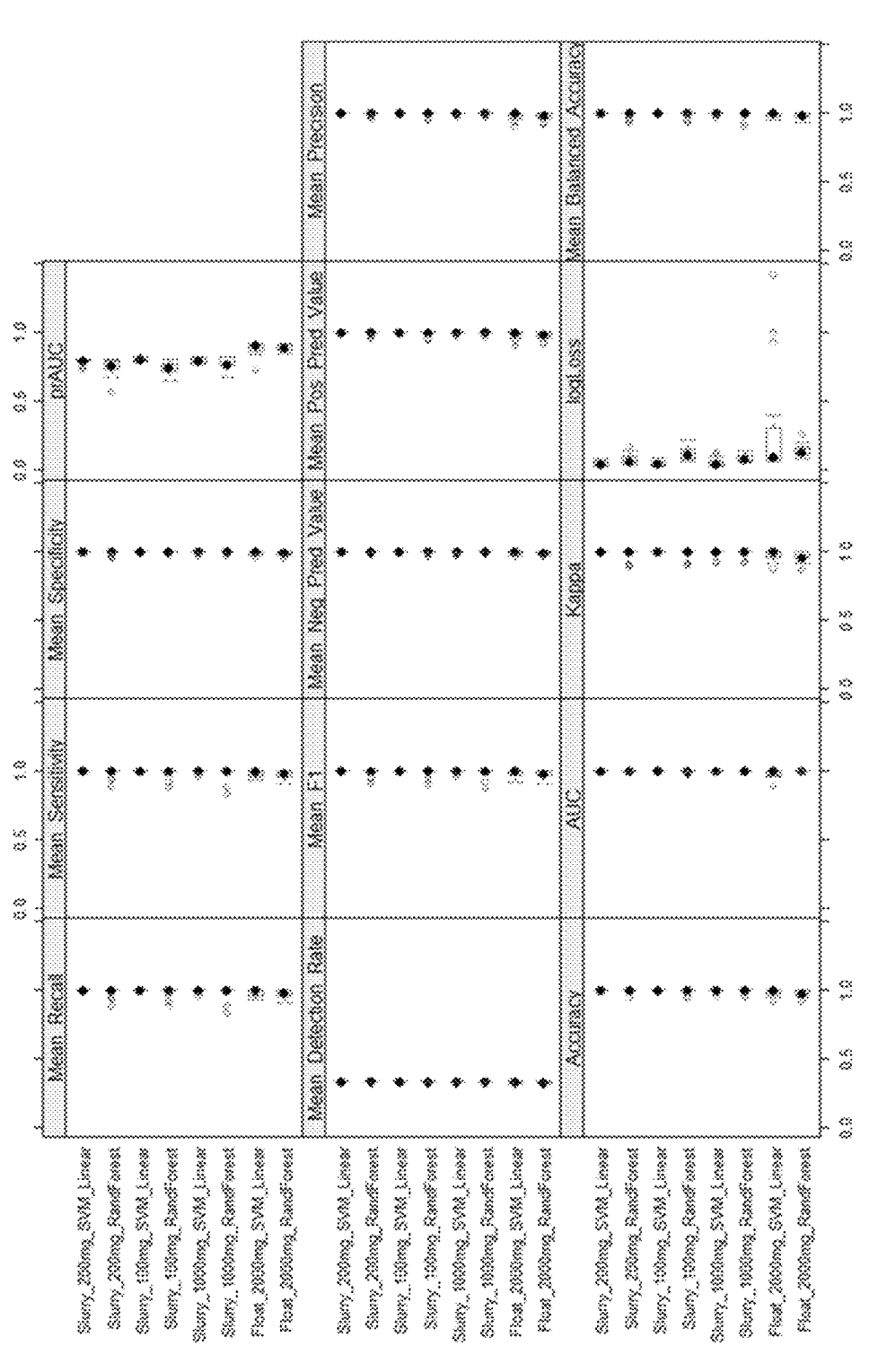
FIG. 2 shows training results for experiments described herein.
Figure 3:
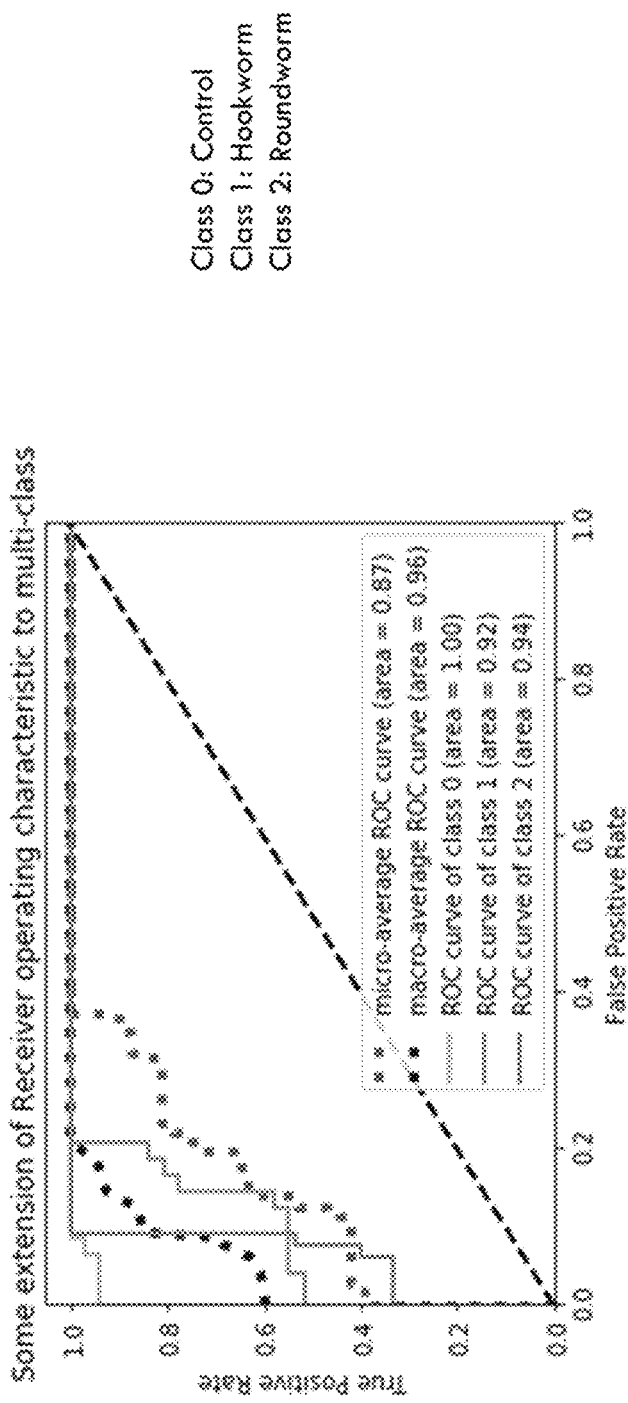
FIG. 3 shows a multiclass ROC curve for analysis of a slurry sample comprising 100 mg of sample.
Figure 4:
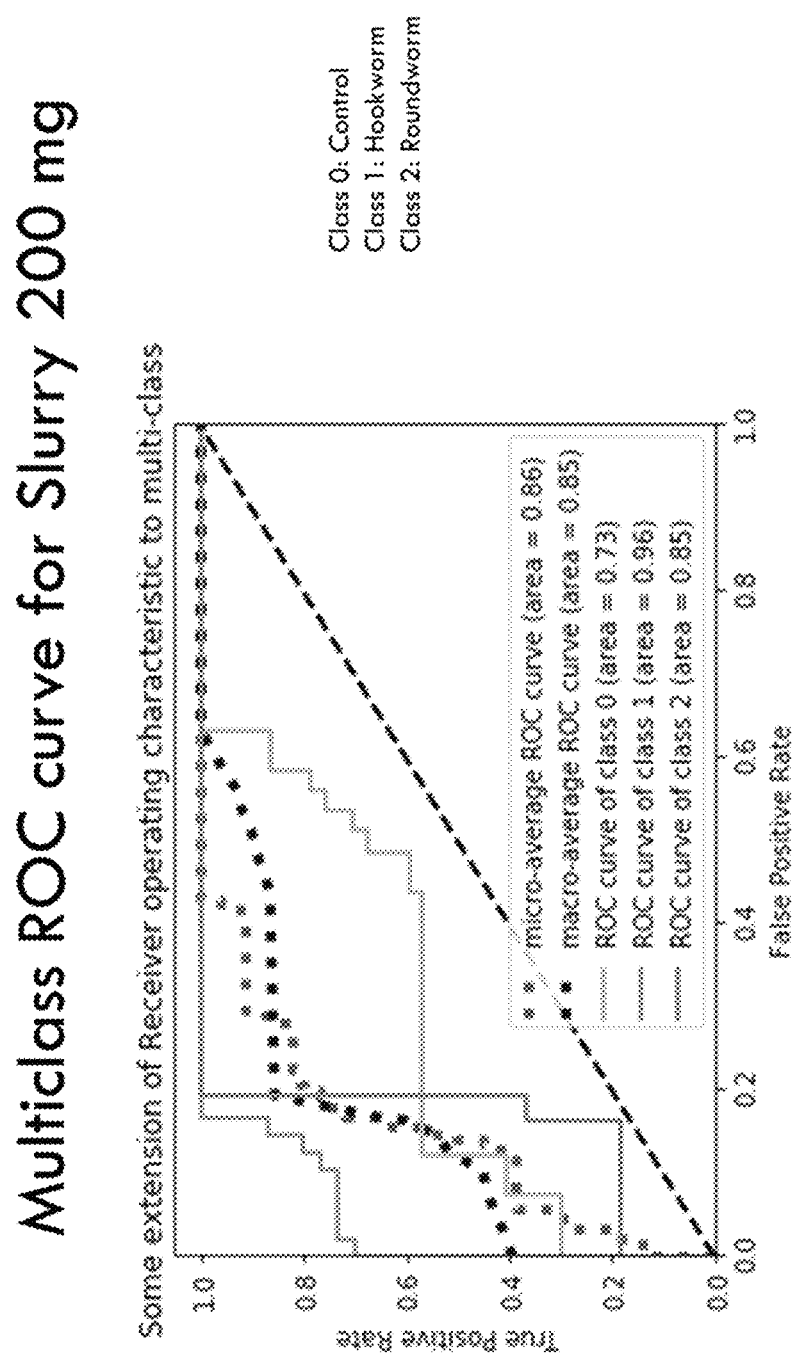
FIG. 4 shows a multiclass ROC curve for analysis of a slurry sample comprising 200 mg of sample.
Figure 5:
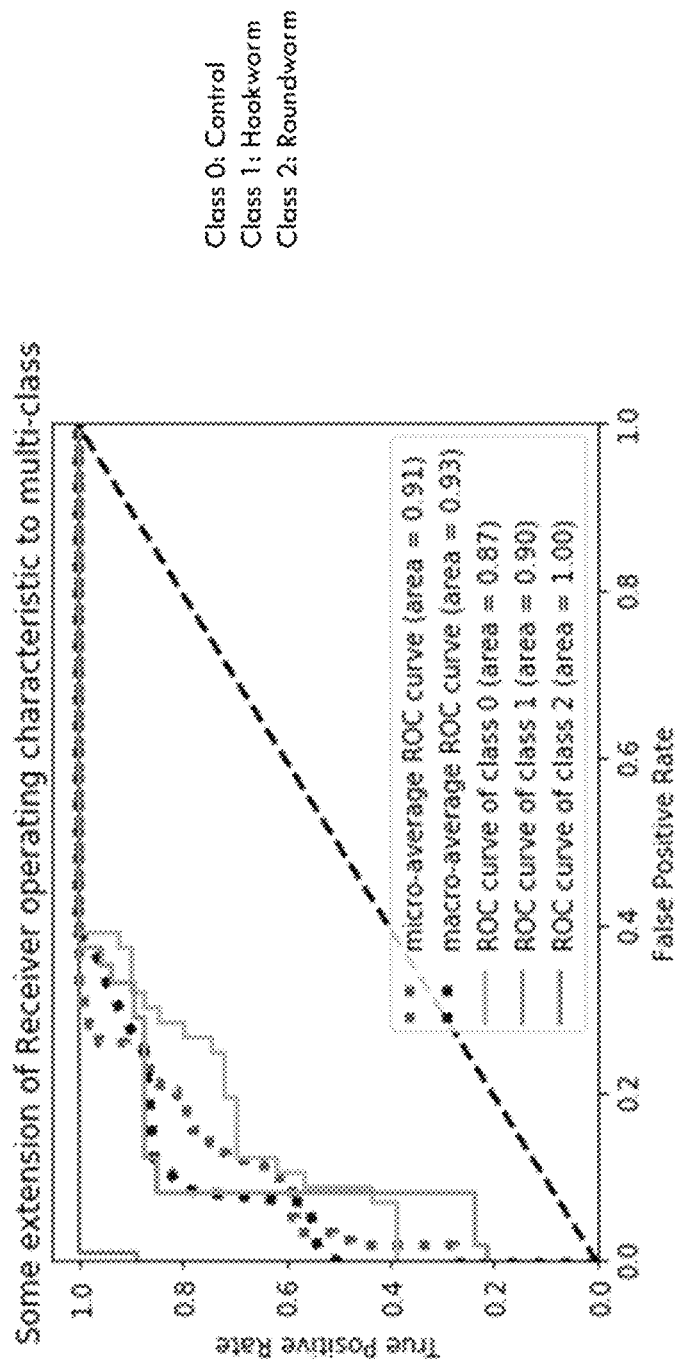
FIG. 5 shows a multiclass ROC curve for analysis of a slurry sample comprising 1000 mg of sample.
Figure 6:
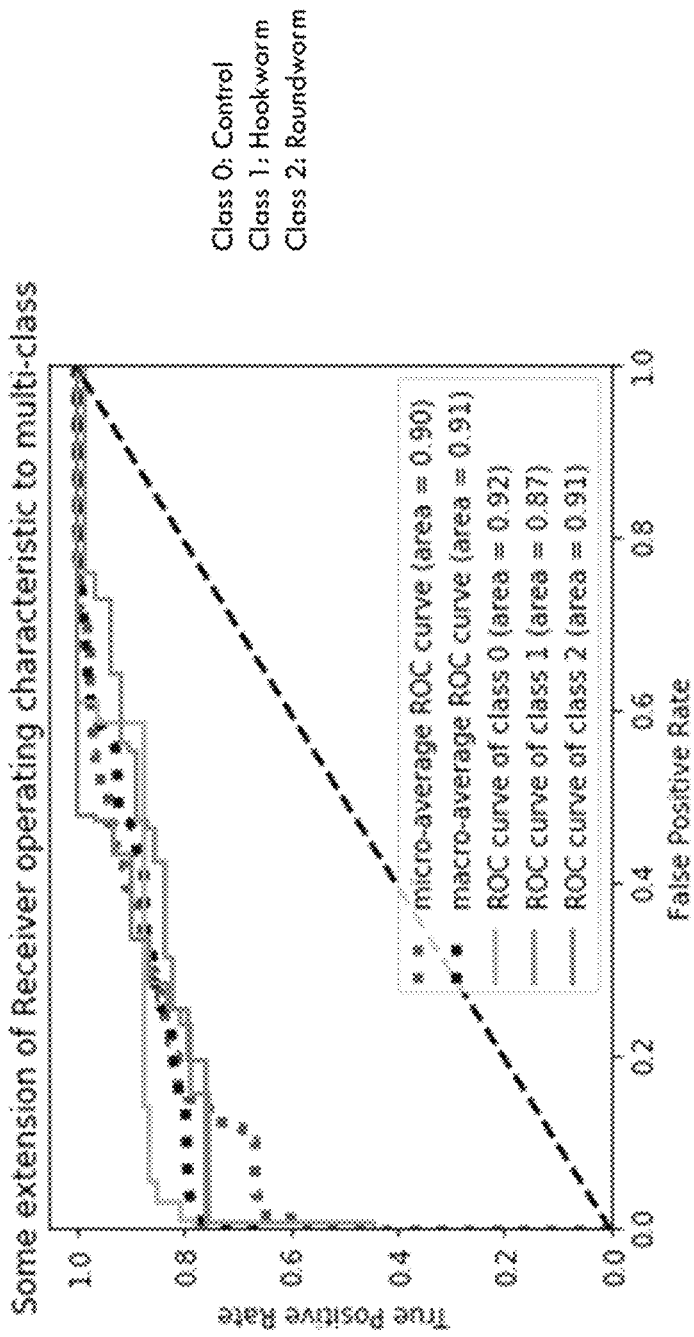
FIG. 6 shows a multiclass ROC curve for analysis of a float sample comprising 2000 mg of sample.

Machine learning models were trained on training data set and their results were validated using testing data sets (FIG. 1B). Training results are shown in FIG. 2.

Testing results are shown in Table 2 and FIGS. 3-6. FIGS. 3-6 show Receiver Operating Characteristic (ROC) curves. ROC is a graphical plot that illustrates the diagnostic ability of a binary classifier system as its discrimination threshold is varied. ROC curves for multiple classes are not typically used. However, the ROC curves described herein were extended for multiple classes by using a micro-averaging method. This method gives equal weight to the classification of each label. This is done by considering each element of the label indicator matrix as a binary prediction (micro-averaging). This approach was applied to the fecal parasite class Raman spectra results.

The results demonstrate that sample sizes as small as 100 mg can be tested using the described Raman spectroscopy methods.

TABLE 1

| Control | Runs | Hookworm | Runs | Roundworm | Runs |
|---|---|---|---|---|---|
| BMF181 100 mg Slurry | 20 | BMF177 100 mg Slurry | 15 | BMF180 100 mg Slurry | 20 |
| BMF181 200 mg Slurry | 20 | BMF177 200 mg Slurry | 15 | BMF180 200 mg Slurry | 20 |
| BMF181 1000 mg Slurry | 20 | BMF177 1000 mg Slurry | 15 | BMF180 1000 mg Slurry | 20 |
| BMF181 2000 mg Float | 50 | BMF177 2000 mg Float | 50 | BMF180 2000 mg Float | 50 |
| BMF184 100 mg Slurry | 25 | BMF188 100 mg Slurry | 25 | BMF185 100 mg Slurry | 15 |
| BMF184 200 mg Slurry | 25 | BMF188 200 mg Slurry | 25 | BMF185 200 mg Slurry | 10 |
| BMF184 1000 mg Slurry | 26 | BMF188 1000 mg Slurry | 50 | BMF185 1000 mg Slurry | 5 |
| BMF184 2000 mg Float | 50 | BMF188 2000 mg Float | 50 | BMF185 2000 mg Float | 25 |
| BMF194 100 mg Slurry | 20 | BMF189 100 mg Slurry | 10 | BMF186 100 mg Slurry | 10 |
| BMF194 200 mg Slurry | 20 | BMF189 200 mg Slurry | 10 | BMF186 200 mg Slurry | 10 |
| BMF194 1000 mg Slurry | 20 | BMF189 1000 mg Slurry | 50 | BMF186 1000 mg Slurry | 10 |
| BMF194 2000 mg Float | 20 | BMF189 2000 mg Float | 25 | BMF186 2000 mg Float | 25 |
| BMF195 100 mg Slurry | 20 | BMF190 100 mg Slurry | 12 | | |
| BMF195 200 mg Slurry | 20 | BMF190 200 mg Slurry | 12 | | |
| BMF195 1000 mg Slurry | 20 | BMF190 1000 mg Slurry | 10 | | |
| BMF195 2000 mg Float | 50 | BMF190 2000 mg Float | 20 | | |
| BMF198 100 mg Slurry | 25 | BMF196 100 mg Slurry | 25 | | |
| BMF198 200 mg Slurry | 25 | BMF196 200 mg Slurry | 25 | | |
| BMF198 1000 mg Slurry | 25 | BMF196 1000 mg Slurry | 25 | | |
| BMF198 2000 mg Float | 25 | BMF196 2000 mg Float | 48 | | |
| BMF199 100 mg Slurry | 20 | | | | |
| BMF199 200 mg Slurry | 20 | | | | |
| BMF199 1000 mg Slurry | 20 | | | | |
| BMF199 2000 mg Float | 50 | | | | |

TABLE 2

| | Accuracy | Kappa | Sensitivity | Specificity |
|---|---|---|---|---|
| Slurry 100 mg, SVM Linear Kernel | 98.7% | 0.98 | 97.1% | 100% |
| Slurry 200 mg, SVM Linear Kernel | 100% | 1 | 100% | 100% |
| Slurry 100o mg, SVM Linear Kernel | 100% | 1 | 100% | 100% |
| Float 2000 mg, SVM Linear Kernel | 98.8% | 0.98 | 100% | 96.6% |
| Slurry 100 mg, SVM Random Forest | 97.4% | 0.96 | 94 1% | 100% |
| Slurry 200 mg, SVM Random Forest | 97.4% | 0.96 | 93.500 | 100% |
| Slurry 1000 mg, SVM Random Forest | 109% | 1 | 100% | 100% |
| Float 2000 mg, SVM Random Forest | 109% | 1 | 100% | 100% |

All publications, patents and patent applications mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

We claim:

1. A method of identifying the presence of a parasite in a fecal sample from a subject, comprising:
   a) diluting said sample to generate a diluted sample, wherein said sample comprises less than 1 gram of feces; and
   b) obtaining a Raman spectrum of said sample using a Raman spectrometer, wherein said Raman spectrum identifies the presence of a parasite in said sample, wherein said presence of a parasite in said sample is determined based on the presence of parasite specific coproantigens in said sample.

2. The method of claim 1, wherein said feces sample comprises 100-200 mg feces.

3. The method of claim 2, wherein said feces sample comprises 100 mg feces.

4. The method of claim 1, wherein said Raman spectroscopy utilizes internal reflective amplification.

5. The method of claim 1, wherein said Raman spectroscopy generates a molecular fingerprint of said sample.

6. The method of claim 5, wherein said molecular fingerprint comprises spectral bands indicative of said coprantigens.

7. The method of claim 5, wherein said molecular fingerprint identifies the genus, species, or strain of parasite in said sample.

8. The method of claim 7, wherein said parasite is selected from the group consisting of hookworm, roundworm, Cystoisospora, Giardia, and whipworm.

9. The method of claim 1, wherein said Raman spectrum are analyzed using a machine learning algorithm.

10. The method of claim 9, wherein said machine learning algorithm is support vector machine and/or random forest algorithms.

11. The method of claim 1, wherein said Raman spectrum are pre-processed prior to said analysis using a machine learning algorithm.

12. The method of claim 11, wherein said pre-processing comprising one or more of morphology-split background subtraction and unit vector normalization.

13. The method of claim 1, wherein said method further comprises generating a receiver operating characteristic curve (ROC) for multiple classes.

14. The method of claim 13, wherein said ROC comprises a micro-averaging step.

15. A method of treating a parasitic infection in a canine subject, comprising:
   a) detecting the presence of a parasitic infection in a sample from said canine subject using a method of claim 1; and
   b) administering an antibiotic to said canine subject.

16. A system or kit comprising:
   a) a diluted fecal mixture from a subject, wherein said diluted fecal mixture comprises a fecal sample and a liquid comprising water, wherein said fecal sample comprises less than one gram of feces;
   b) a Raman spectrometer; and
   c) a computer system comprising a computer memory and computer processor, wherein said computer memory comprises a library of Raman spectrometric signatures from antigens from parasites, and algorithm for comparing a Raman spectrometric signature from said sample to said library, wherein said computer system is operably linked to said Raman spectrometer.

* * * * *